United States Patent
McHenry et al.

(10) Patent No.: US 11,950,834 B2
(45) Date of Patent: *Apr. 9, 2024

(54) SYSTEMS AND METHODS FOR DETECTING OPENING OF THE JAWS OF A VESSEL SEALER MID-SEAL

(71) Applicant: Covidien LP, Mansfield, MA (US)

(72) Inventors: Jennifer R. McHenry, Denver, CO (US); Anthony D. Ricke, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1150 days.

This patent is subject to a terminal disclaimer.

(21) Appl. No.: 16/713,724

(22) Filed: Dec. 13, 2019

(65) Prior Publication Data

US 2020/0113617 A1  Apr. 16, 2020

Related U.S. Application Data (63) Continuation of application No. 15/173,023, filed on Jun. 3, 2016, now Pat. No. 10,512,499.

(Continued)

(51) Int. Cl.
*A61B 18/10* (2006.01)
*A61B 18/12* (2006.01)
(Continued)

(52) U.S. Cl.
CPC ...... *A61B 18/1233* (2013.01); *A61B 18/1442* (2013.01); *A61B 18/1445* (2013.01);
(Continued)

(58) Field of Classification Search
CPC .......... A61B 18/1233; A61B 18/1442; A61B 18/1445; A61B 2018/00404;
(Continued)

(56) References Cited

U.S. PATENT DOCUMENTS 7,678,105 B2   3/2010   McGreevy et al.
7,972,334 B2   7/2011   McGreevy et al.
(Continued)

FOREIGN PATENT DOCUMENTS

EP   0696181 A1   2/1996
EP   2510894 A1   10/2012
WO   9424949 A1   11/1994

OTHER PUBLICATIONS

Extended European Search Report, dated Aug. 11, 2016, for corresponding European Patent Application No. 16174916.3; issued by the European Patent Office (8 pages).

(Continued)

*Primary Examiner* — Jaymi E Della
(74) *Attorney, Agent, or Firm* — Carter, DeLuca & Farrell LLP (57) ABSTRACT

Disclosed are systems, devices, and methods for operating an electrosurgical generator, comprising an RF output stage configured to output an electrosurgical waveform through at least one pair of electrodes, sensing circuitry configured to measure an impedance between the at least one pair of electrodes configured to grasp tissue, and a controller configured to determine whether the impedance of the tissue disposed between the at least one pair of electrodes exceeds an impedance threshold, determine whether a change in the impedance is greater than an upper change in impedance threshold, and output an alarm indicative of the at least one pair of electrodes being at least partially open based on at least one of the impedance exceeding the impedance threshold or the change in impedance exceeding the change in impedance threshold.

15 Claims, 5 Drawing Sheets

Related U.S. Application Data (60) Provisional application No. 62/181,902, filed on Jun. 19, 2015.

(51) Int. Cl.
*A61B 18/14* (2006.01)
*A61B 18/00* (2006.01)

(52) U.S. Cl.
CPC ............... *A61B 2018/00404* (2013.01); *A61B 2018/0063* (2013.01); *A61B 2018/00666* (2013.01); *A61B 2018/00869* (2013.01); *A61B 2018/00875* (2013.01); *A61B 2018/00898* (2013.01)

(58) Field of Classification Search
CPC .. A61B 2018/0063; A61B 2018/00666; A61B 2018/00869; A61B 2018/00875; A61B 2018/00898
See application file for complete search history.

(56) References Cited

U.S. PATENT DOCUMENTS

| | | |
|---|---|---|
| 7,972,335 B2 | 7/2011 | McGreevy et al. |
| 8,343,144 B2 | 1/2013 | Kleyman |
| 8,357,158 B2 | 1/2013 | McKenna et al. |
| 8,740,901 B2 | 6/2014 | Johnson et al. |
| 8,764,749 B2 | 7/2014 | McKenna et al. |
| 9,186,200 B2 | 11/2015 | Unger et al. |
| 2008/0262489 A1 | 10/2008 | Steinke |
| 2010/0179538 A1 | 7/2010 | Podhajsky |
| 2012/0078139 A1 | 3/2012 | Aldridge et al. |
| 2012/0101413 A1 | 4/2012 | Beetel |
| 2012/0136347 A1 | 5/2012 | Brustad et al. |
| 2012/0283731 A1 | 11/2012 | Unger et al. |
| 2013/0304066 A1 | 11/2013 | Kerr et al. |
| 2015/0272657 A1 | 10/2015 | Yates |

OTHER PUBLICATIONS

Extended European Search Report, issued by the European Patent Office, for corresponding European Patent Application No. 16174916.3, dated Aug. 11, 2016 (8pages).

SYSTEMS AND METHODS FOR DETECTING OPENING OF THE JAWS OF A VESSEL SEALER MID-SEAL

CROSS-REFERENCE TO RELATED APPLICATION

The present application is a continuation of U.S. patent application Ser. No. 15/173,023, filed Jun. 3, 2016, now U.S. Pat. No. 10,512,499, which claims the benefit of and priority to U.S. Provisional Patent Application No. 62/181,902, filed on Jun. 19, 2015. The entire contents of all of the foregoing applications are incorporated by reference herein.

BACKGROUND

Technical Field

The present disclosure relates to electrosurgical systems and methods for performing electrosurgical procedures. More particularly, the present disclosure relates to systems and methods for sealing tissue using electrosurgical forceps and for detecting whether the jaws of a vessel sealer are open during a sealing procedure.

Background of Related Art

Electrosurgery involves application of high radio frequency electrical current to a surgical site to cut, ablate, or coagulate tissue. In monopolar electrosurgery, a source or active electrode delivers radio frequency alternating current from the electrosurgical generator to the targeted tissue. A patient return electrode is placed remotely from the active electrode to conduct the current back to the generator.

In bipolar electrosurgery, return and active electrodes are placed in close proximity to each other such that an electrical circuit is formed between the two electrodes (e.g., in the case of an electrosurgical forceps). In this manner, the applied electrical current is limited to the body tissue positioned between the electrodes. Accordingly, bipolar electrosurgery generally involves the use of instruments where it is desired to achieve a focused delivery of electrosurgical energy between two electrodes positioned on the instrument, e.g. forceps or the like. Electrosurgical procedures outlined above may utilize various tissue and energy parameters in a feedback-based control system. Bipolar electrosurgery generally involves the use of forceps.

A forceps is a pliers-like instrument which relies on mechanical action between its jaws to grasp, clamp and constrict vessels or tissue. "Open forceps" are commonly used in open surgical procedures whereas "endoscopic forceps" or "laparoscopic forceps" are used for less invasive endoscopic surgical procedures. Electrosurgical forceps (open or endoscopic) use mechanical clamping action and electrical energy to cause hemostasis on the clamped tissue. The forceps include electrosurgically conductive plates which apply electrosurgical energy to the clamped tissue. By controlling the intensity, frequency, and duration of the electrosurgical energy applied through the conductive plates to the tissue, the surgeon can coagulate, cauterize, and/or seal tissue.

During bipolar vessel sealing certain conditions may result in improper energy application. This may occur when bipolar electrodes are separated from one another without contacting tissue, which results in an open circuit or when the bipolar electrodes come in direct contact with each other and/or clamp on a highly conductive material (e.g., a surgical metallic clip or staple). In either of these instances, continual application of energy may result in injury to the patient and/or damage to the electrosurgical generator and other equipment. Thus, there is a need for new and improved systems and methods for detecting and responding to such conditions.

SUMMARY

According to one embodiment, the present disclosure provides for a method for detecting whether the jaws of an electrosurgical instrument are in a slow open condition.

In an aspect of the present disclosure, an electrosurgical generator comprises an RF output stage configured to output an electrosurgical waveform through at least one pair of electrodes, sensing circuitry configured to measure a current of the electrosurgical waveform and an impedance between the at least one pair of electrodes configured to grasp tissue, and a controller configured to determine whether the impedance of the tissue disposed between the at least one pair of electrodes exceeds an impedance threshold, determine whether a change in the impedance is greater than an upper change in impedance threshold, and output an alarm indicative of the at least one pair of electrodes being at least partially open based on at least one of the impedance exceeding the impedance threshold or the change in impedance exceeding the change in impedance threshold.

In another aspect of the present disclosure, the controller is further configured to determine whether the change in impedance is less than a lower change in impedance threshold.

In a further aspect of the present disclosure, the controller is further configured to detect a phase shift of the electrosurgical waveform, determine whether the phase shift exceeds a phase shift threshold, and activate the alarm based on the phase shift determination.

In another aspect of the present disclosure, the controller is further configured to signal the RF output stage to output the electrosurgical waveform for a time period if the change in impedance is between the lower and upper change in impedance thresholds.

In a further aspect of the present disclosure, the controller is further configured to determine whether the phase shift exceeds the phase shift threshold, and activate the alarm if the phase shift exceeds the phase shift threshold.

In an aspect of the present disclosure, a method of detecting whether the jaws of an electrosurgical instrument are in a slow open condition comprises outputting an electrosurgical waveform through at least one pair of electrodes of the electrosurgical instrument, measuring an impedance between the at least one pair of electrodes configured to grasp tissue, and determining whether the impedance of the tissue disposed between the at least one pair of electrodes exceeds an impedance threshold, determining whether a change in the impedance is greater than an upper change in impedance threshold, and outputting an alarm indicative of the at least one pair of electrodes being at least partially open based on at least one of the impedance exceeding the impedance threshold or the change in impedance exceeding the change in impedance threshold.

In another aspect of the present disclosure, the method further comprises determining whether the change in impedance is less than a lower change in impedance threshold.

In a further aspect of the present disclosure, the method further comprises detecting a phase shift of the electrosurgical waveform, determining whether the phase shift exceeds a phase shift threshold, and activating the alarm based on the phase shift determination.

In another aspect of the present disclosure, the method further comprises outputting the electrosurgical waveform for a time period if the change in impedance is between the lower and upper change in impedance thresholds.

In a further aspect of the present disclosure, the method further comprises determining whether the phase shift exceeds the phase shift threshold, and activating the alarm if the phase shift exceeds the phase shift threshold.

In an aspect of the present disclosure, a non-transitory computer-readable storage medium stores instructions which, when executed by a processor, cause an electrosurgical generator to output an electrosurgical waveform through at least one pair of electrodes of an electrosurgical instrument, measure an impedance between the at least one pair of electrodes configured to grasp tissue, determine whether the impedance of the tissue disposed between the at least one pair of electrodes exceeds an impedance threshold, determine whether a change in the impedance is greater than an upper change in impedance threshold, and output an alarm indicative of the at least one pair of electrodes being at least partially open based on at least one of the impedance exceeding the impedance threshold or the change in impedance exceeding the change in impedance threshold.

In another aspect of the present disclosure, the instructions further cause the electrosurgical generator to determine whether the change in impedance is less than a lower change in impedance threshold.

In a further aspect of the present disclosure, the instructions further cause the electrosurgical generator to detect a phase shift of the electrosurgical waveform, determine whether the phase shift exceeds a phase shift threshold, and activate the alarm based on the phase shift determination.

In another aspect of the present disclosure, the instructions further cause the electrosurgical generator to output the electrosurgical waveform for a time period if the change in impedance is between the lower and upper change in impedance thresholds.

In a further aspect of the present disclosure, the instructions further cause the electrosurgical generator to determine whether the phase shift exceeds the phase shift threshold, and activate the alarm if the phase shift exceeds the phase shift threshold.

BRIEF DESCRIPTION OF THE DRAWINGS

Various embodiments of the present disclosure are described herein with reference to the drawings wherein.

DETAILED DESCRIPTION

Particular embodiments of the present disclosure will be described below with reference to the accompanying drawings. In the following description, well-known functions or constructions are not described in detail to avoid obscuring the present disclosure in unnecessary detail. Those skilled in the art will understand that the present disclosure may be adapted for use with either an endoscopic instrument, a laparoscopic instrument, or an open instrument. It should also be appreciated that different electrical and mechanical connections and other considerations may apply to each particular type of instrument.

A generator according to the present disclosure can perform monopolar and/or bipolar electrosurgical procedures, including, for example, cutting, coagulation, ablation, and vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cut, blend, coagulate, division with hemostasis, fulgurate, spray, etc.) and procedures (e.g., monopolar, bipolar, vessel sealing). In embodiments, the generator may be embedded, integrated or otherwise coupled to the electrosurgical instruments providing for an all-in-one electrosurgical apparatus.

Figure 1:
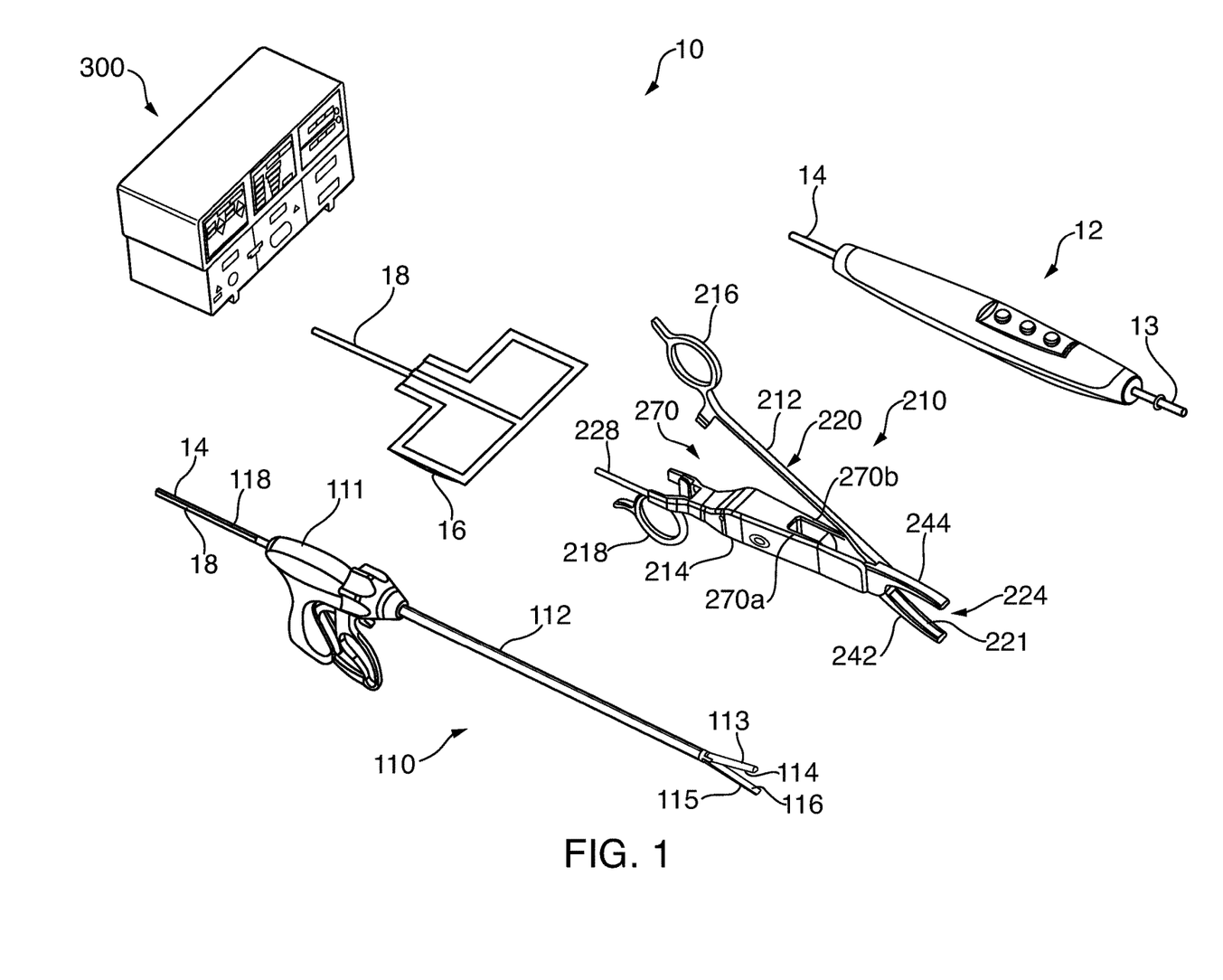
FIG. 1 is a perspective view of the components of an embodiment of an electrosurgical system according to the present disclosure.

FIG. 1 is an illustration of a monopolar and bipolar electrosurgical system 10 according to the present disclosure. The system 10 may include one or more monopolar electrosurgical instruments 12 having one or more active electrodes 13 (e.g., electrosurgical cutting probe, ablation electrodes, etc.) for treating tissue of a patient. Electrosurgical alternating current is supplied to the instrument 12 by a generator 300 via a supply line 14 that is connected to an active terminal 330 (FIG. 3) of the generator 300, allowing the instrument 12 to cut, coagulate, ablate, and/or otherwise treat tissue. The alternating current is returned to the generator 300 through a return electrode pad 16 via a return line 18 at a return terminal 332 (FIG. 3) of the generator 300. For monopolar operation, the system 10 may include a plurality of return electrode pads 16 that, in use, are disposed on a patient to minimize the chances of tissue damage by maximizing the overall contact area with the patient. In addition, the generator 300 and the return electrode pads 16 may be configured for monitoring so-called "tissue-to-patient" contact to ensure that sufficient contact exists between the return electrode pads 16 and the tissue to further minimize chances of tissue damage.

The system 10 may also include one or more bipolar electrosurgical instruments, for example, a bipolar electrosurgical forceps 110 or a bipolar electrosurgical forceps 210 having one or more electrodes for treating tissue of a patient. The bipolar electrosurgical instruments 110, 210 may be used with open and/or laparoscopic surgical procedures.

Figure 3:
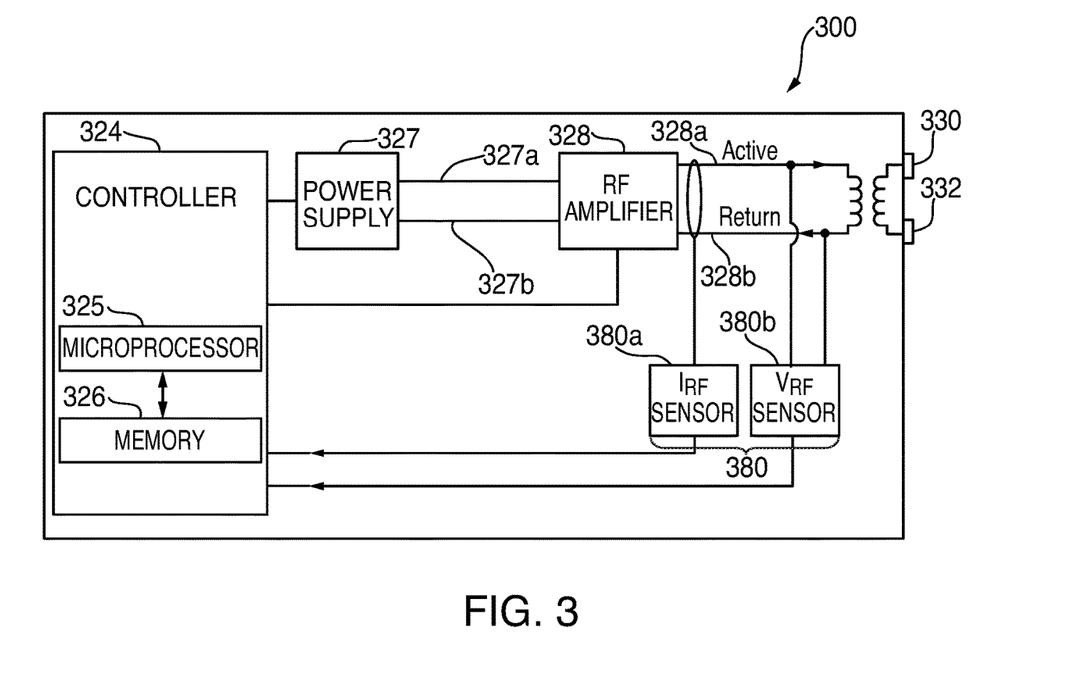
FIG. 3 is a schematic, block diagram of the embodiment of the electrosurgical generator of FIG. 1 according to the present disclosure.

The bipolar electrosurgical forceps 110 includes housing 111 and opposing jaw members 113 and 115 disposed at a distal end of a shaft 112. The jaw members 113 and 115 have one or more active electrodes 114 and a return electrode 116 disposed therein, respectively. The active electrode 114 and the return electrode 116 are connected to the generator 300 through cable 118 that includes the supply and return lines 14, 18 coupled to the active and return terminals 330, 332, respectively (FIG. 3). The electrosurgical forceps 110 is coupled to the generator 300 at a connector having connections to the active and return terminals 330, 332 (e.g., pins) via a plug disposed at the end of the cable 118, wherein the plug includes contacts from the supply and return lines 14, 18 as described in more detail below.

The bipolar electrosurgical forceps 210 includes a mechanical forceps 220 having an end effector 224 and a disposable electrode assembly 221. Mechanical forceps 220 includes first and second elongated shaft members 212, 214. Disposed at the proximal end portions of shaft members 212, 214 are handle members 216, 218, respectively, that are configured to allow a user to effect movement of at least one of the shaft members 212, 214 relative to the other. The end effector 224 includes opposing jaw members 242, 244 that extend from the distal end portions of shaft members 212, 214, respectively. The jaw members 242, 244 are movable relative to each other in response to movement of shaft members 212, 214. A housing 270 having a pair of housing halves 270a, 270b is configured to matingly engage and releasably encompass at least a portion of shaft member 214. Forceps 210 includes an electrical cable 228 extending from housing 270 configured to electrically connect forceps 210 to a source of electrosurgical energy, such as electrosurgical generator 300.

Bipolar electrosurgical forceps 110 is substantially similar to bipolar electrosurgical forceps 210 except that bipolar electrical forceps 110 is configured for laparoscopic and/or endoscopic surgical procedures whereas bipolar electrosurgical forceps 210 is configured for open surgical procedures.

Figure 2:
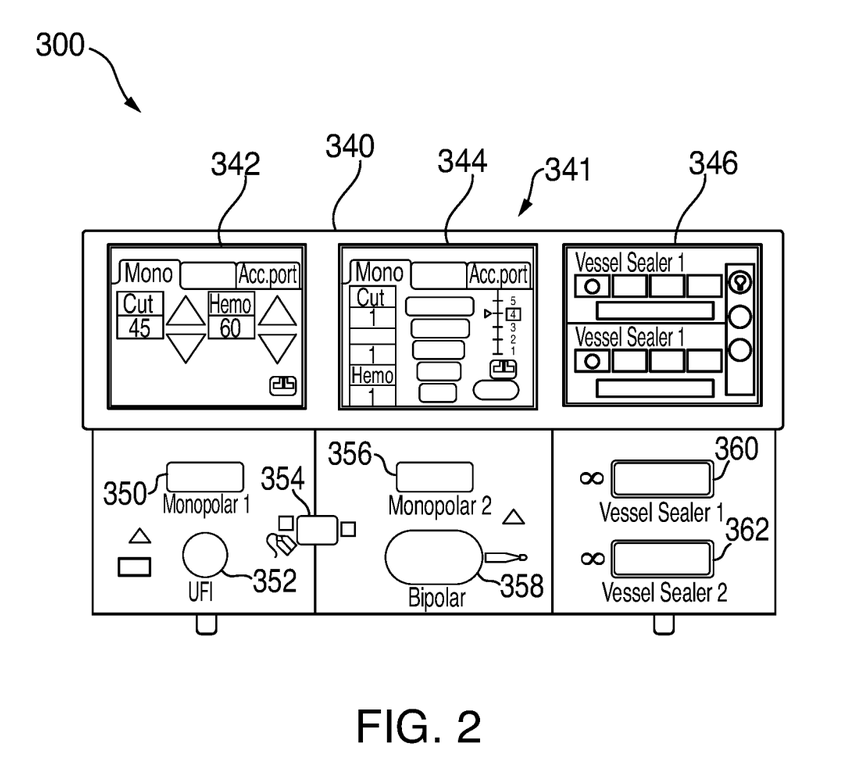
FIG. 2 is a front view of an embodiment of an electrosurgical generator of FIG. 1 according to the present disclosure.

With reference to FIG. 2, a front face 340 of the generator 300 is shown. The generator 300 may be any suitable type (e.g., electrosurgical, microwave, etc.) and may include a plurality of connectors 350-362 to accommodate various types of electrosurgical instruments (e.g., bipolar electrosurgical forceps 110, etc.).

The generator 300 includes a user interface 341 having one or more display screens or information panels 342, 344, 346 for providing the user with a variety of output information (e.g., intensity settings, treatment complete indicators, etc.). Each of the screens 342, 344, 346 is associated with corresponding connector 350-362. The generator 300 includes suitable input controls (e.g., buttons, activators, switches, touch screen, etc.) for controlling the generator 300. The display screens 342, 344, 346 are also configured as touch screens that display a corresponding menu for the electrosurgical instruments (e.g., bipolar electrosurgical forceps 110, etc.). The user then adjusts inputs by simply touching corresponding menu options.

Screen 342 controls the monopolar output and the devices connected to the connectors 350 and 352. Connector 350 is configured to couple to a monopolar electrosurgical instrument (e.g., monopolar electrosurgical instrument 12) and connector 352 is configured to couple to a foot switch (not shown). The foot switch provides for additional inputs (e.g., replicating inputs of the generator 300). Screen 344 controls monopolar and bipolar output and the devices connected to the connectors 356 and 358. Connector 356 is configured to couple to other monopolar instruments. Connector 358 is configured to couple to a bipolar instrument (e.g., bipolar electrosurgical forceps 110, 210, etc.).

Screen 346 controls bipolar sealing procedures performed by the bipolar electrosurgical forceps 110 that may be plugged into the connectors 360 and 362. The generator 300 outputs energy through the connectors 360 and 362 suitable for sealing tissue grasped by the bipolar electrosurgical forceps 110. In particular, screen 346 outputs a user interface that allows the user to input a user-defined intensity setting. The user-defined setting may be any setting that allows the user to adjust one or more energy delivery parameters, such as power, current, voltage, energy, etc., or sealing parameters, such as energy rate limiters, sealing duration, etc. The user-defined setting is transmitted to the controller 324 where the setting may be saved in memory 326. In embodiments, the intensity setting may be a number scale, such as, for example, from one to ten or one to five. In embodiments, the intensity setting may be associated with an output curve of the generator 300. The intensity settings may be specific for each bipolar electrosurgical forceps 110 being utilized, such that various instruments provide the user with a specific intensity scale corresponding to the bipolar electrosurgical forceps 110.

FIG. 3 shows a schematic block diagram of the generator 300 configured to output electrosurgical energy. The generator 300 includes a controller 324, a power supply 327, and a radio frequency (RF) amplifier (e.g., an RF output stage) 328. The power supply 327 is a high voltage, direct current (DC) power supply connected to an alternating current (AC) source (e.g., line voltage). The power supply 327 provides high voltage, DC power to the RF amplifier 328 via leads 327a and 327b. The RF amplifier 328 converts the high voltage, DC power into treatment energy (e.g., electrosurgical) and delivers the treatment energy to the active terminal 330. The electrosurgical energy may be RF current. The treatment energy is returned to the RF amplifier 328 via the return terminal 332. The active and return terminals 330 and 332 are coupled to the RF amplifier 328 through an isolation transformer 329.

The RF amplifier 328 is configured to operate in a plurality of modes, during which the generator 300 outputs corresponding waveforms having specific duty cycles, peak voltages, crest factors, etc. It is envisioned that in other embodiments, the generator 300 may be based on other types of suitable power supply topologies.

The controller 324 includes a processor 325 operably connected to a memory 326, which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor 325 may include one or more of a microprocessor, a digital signal processor (DSP), an application specific integrated circuit (ASIC), a field-programmable gate array (FPGA), or discrete logic circuitry. The processor 325 includes an output port that is operably connected to the power supply 327 and/or RF amplifier 328 allowing the processor 325 to control the output of the generator 300 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 324. The controller 324 then sends control signals to the power supply 327 and/or RF amplifier 328 to adjust the high voltage, DC power and/or the RF current, respectively. Those skilled in the art will appreciate that the processor 325 may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof.

The generator 300 according to the present disclosure includes a plurality of sensors 380, e.g., an RF current sensor 380a and an RF voltage sensor 380b. Various components of the generator 300, including the RF amplifier 328 and the RF current and voltage sensors 380a and 380b, may be disposed on a printed circuit board (PCB). The RF current sensor 380a is coupled to the active terminal 230 and provides measurements of the RF current supplied by the RF amplifier 328. The RF voltage sensor 380b is coupled to the active and return terminals 330 and 332, and provides measurements of the RF voltage supplied by the RF amplifier 328. In embodiments, the RF current and voltage sensors 380a and 380b may be coupled to active and return leads 328a and 328b, which interconnect the active and return terminals 330 and 332 to the RF amplifier 328, respectively.

The RF current and voltage sensors 380a and 380b provide the sensed RF voltage and current signals, respectively, to the controller 324, which then may adjust the output of the power supply 327 and/or the RF amplifier 328 in response to the sensed RF voltage and current signals. The controller 324 also receives input signals from the input controls of the generator 300, the monopolar electrosurgical instrument 12, and/or the bipolar electrosurgical forceps 110. The controller 324 uses the input signals to adjust power output from the generator 300 and/or to perform other control functions.

To achieve an effective tissue seal, the tissue sealing systems and methods of the present disclosure control any combination of the following parameters: (1) the intensity, frequency, and/or duration of the electrosurgical energy applied to the tissue through the active electrodes 114, 116; (2) the pressure applied between the opposing jaw members 113, 115, respectively; and (3) the gap distance between opposing active electrodes 114, 116 during the sealing process. A detailed description of exemplary electrosurgical sealing devices and methods that control the pressure and gap distance are found, for example, in U.S. Pat. No. 7,972,328, the entire contents of which is incorporated herein by reference.

Figure 4:
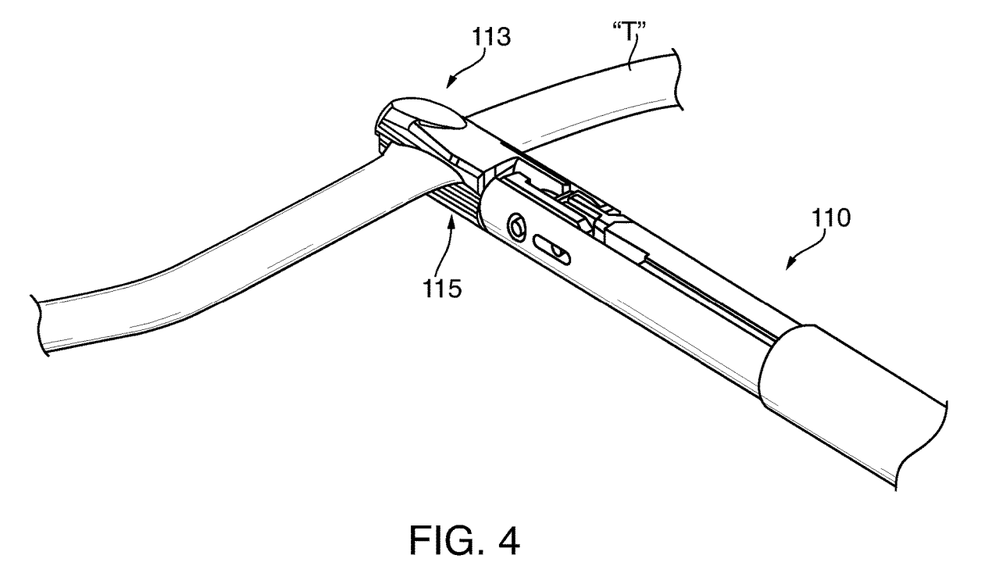
FIG. 4 is a rear, perspective view of an end effector of a bipolar forceps of FIG. 1 shown grasping tissue.

Since the bipolar electrosurgical forceps 110 apply electrosurgical energy through electrodes, each of the jaw members 113, 115 includes a pair of electrically conductive sealing plates 114, 116, respectively, disposed on respective inner-facing surfaces of the jaw members 113, 115. Thus, once the jaw members 113, 115 grasp and clamp the tissue, the bipolar electrosurgical forceps 110 is ready for selective application of electrosurgical energy as illustrated in FIG. 4. At that point, the electrically conductive sealing plates 114, 116 cooperate to seal the tissue "T" held between the electrically conductive sealing plates 114, 116 upon the application of electrosurgical energy.

The system 10 according to the present disclosure regulates the application of electrosurgical energy to achieve an effective tissue seal capable of withstanding high burst pressure. The generator 300 applies electrosurgical energy to tissue. Energy application is regulated by the controller 324 according to an algorithm stored within the memory 326. The algorithm maintains electrosurgical energy supplied to the tissue at constant voltage and varies the output power and/or current based on the type of tissue being sealed. For instance, thicker tissue typically needs more power, whereas thinner tissue needs less power. Therefore, the algorithm adjusts the output power based on tissue type by modifying various variables of the output power (e.g., voltage being maintained, duration of power application, etc.).

The algorithm continually monitors the output power and may generate an alarm in response to an indication that the jaws of an electrosurgical instrument, such as bipolar electrosurgical forceps 110 and/or bipolar electrosurgical forceps 210, are in a slow open condition. A slow open condition occurs when the jaws of the electrosurgical instrument are opened at a sufficiently slow rate to avoid triggering an open circuit alarm while electrosurgical energy is still supplied to the electrodes of the jaw members, e.g., in response to activation of a hand switch or a foot switch. In such an instance, the jaws are not detected to be in an "open" state, and power continues to flow to the jaws, which is problematic for multiple reasons described above. Various systems and methods are contemplated by the present disclosure for determining whether the jaws of the electrosurgical instrument are in a slow open condition. Some methods, as described in more detail below, evaluate impedance (Z), a change in impedance, which is expressed as a non-causal derivative of the impedance, dZ, and/or a rate of change of impedance, which is expressed as the derivative of the impedance over time, dZ/dt. As used herein, non-causal derivative denotes a derivative taken at a center-point of an envelope of a predetermined time period, which may be from about 1 ms to about 100 ms, in embodiments, may be about 10 ms.

Figure 5:
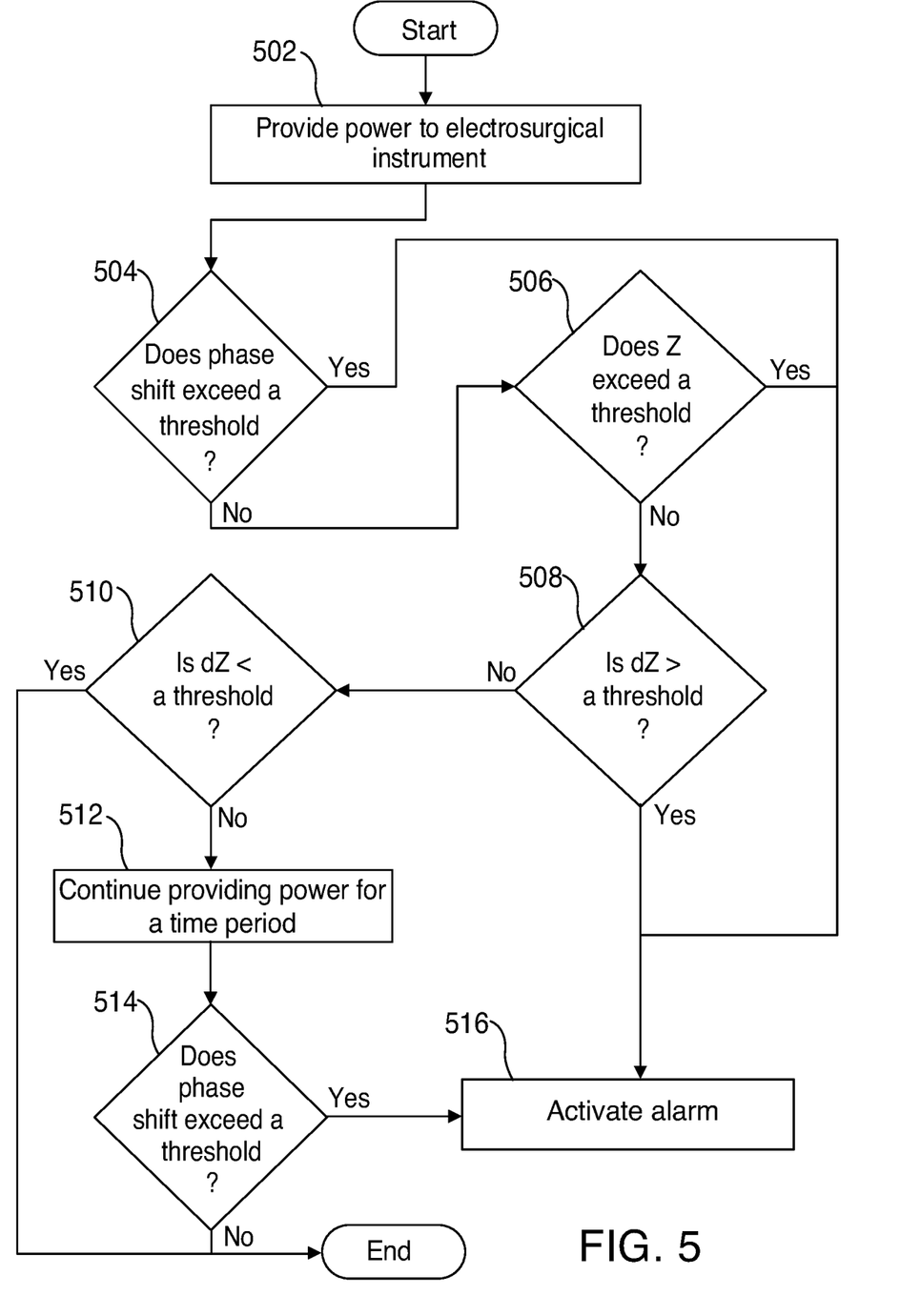
FIG. 5 is a flow chart of a method of detecting an open circuit according to an embodiment of the present disclosure.

Referring now to FIG. 5, a flowchart of a method according to the present disclosure for detecting a slow open condition in electrosurgical system 10 is shown. Starting at step 502, power is provided to an electrosurgical instrument, such as bipolar electrosurgical forceps 110 and/or bipolar electrosurgical forceps 210. At step 504, the controller 324 determines whether there is a phase shift between voltage and current waveforms of the electrosurgical waveform supplied to the electrosurgical instrument that exceeds a predetermined phase shift threshold. In embodiments, the phase shift threshold may be from about 1.3 to about 1.7 radians, in embodiments, from about 1.4 to about 1.6 radians. The phase shift indicates that the jaws of the electrosurgical instrument are in a slow open condition. If the phase shift exceeds the predetermined phase shift threshold, the process proceeds to step 516 where an alarm is activated. If the phase shift is less than the predetermined phase shift threshold, the process continues to step 506, to perform additional verification steps indicative of the slow open condition.

At step 506, the controller 324 determines whether impedance (Z) of the tissue is greater than a impedance threshold. In embodiments, the impedance threshold may be about 2500Ω or more. If the controller 324 determines that Z exceeds the impedance threshold, this may also indicate that the jaws of the electrosurgical instrument are in a slow open condition. Alternatively, if a period of time during which the sealing process was expected to have been completed has expired, and Z exceeds the expected an end impedance threshold (endZ) by a predetermined offset, this may also indicate that the jaws of the electrosurgical instrument are in a slow open condition. The expected end impedance may be preprogrammed and stored in memory 326 of the generator 300. The memory 326 may store a plurality of end impedance values that are selected by the generator 300 based on the instrument and/or tissue being used. In embodiments, the offset impedance may be about 1500Ω or more. If Z is greater than the sum of endZ and the offset, the process proceeds to step 516 where an alarm is activated. If Z does not exceed the sum of endZ and the offset, the process proceeds to step 508.

At step 508, controller 324 calculates dZ and determines whether dZ is greater than an upper dZ threshold. If the controller 324 determines that dZ exceeds the upper dZ threshold, this also indicates that the jaws of the electrosurgical instrument are in a slow open condition. If dZ is greater than the upper dZ threshold, the process proceeds to step 516 where an alarm is activated. If dZ does not exceed the upper dZ threshold, the process proceeds to step 510.

At step 510, the controller 324 determines whether the calculated dZ is less than a lower dZ threshold. If the controller 324 determines that the calculated dZ is less than the lower dZ threshold, this indicates that the sealing process is complete and the process ends. If dZ is not less than the lower dZ threshold, that signifies that dZ is between the first and lower dZ thresholds which indicates that the sealing process is approximating completion, and the process proceeds to step 512.

At step 512, system 10 continues to supply power to the electrosurgical instrument for a predetermined time, which may be about 100 ms, to allow the sealing process to complete, namely, until measured Z reaches the end impedance.

Thereafter, at step 514, the controller 324 performs the same determination as in step 504 above and determines whether the phase shift exceeding the phase shift threshold. If the phase shift exceeds the phase shift threshold, the process proceeds to step 516 where an alarm is activated. If the phase shift does not exceed the phase shift, the seal is complete, and the process ends.

While several embodiments of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator, comprising:
   a radiofrequency (RF) output stage configured to output an electrosurgical waveform through at least one pair of electrodes configured to grasp tissue;
   a sensor configured to measure an impedance between the at least one pair of electrodes; and
   a controller configured to:
      determine whether the impedance of the tissue disposed between the at least one pair of electrodes exceeds an impedance threshold and whether a change in the impedance is greater than an upper change in impedance threshold;
      output an alarm indicative of the at least one pair of electrodes being at least partially open based on the impedance exceeding the impedance threshold and the change in impedance exceeding the upper change in impedance threshold; and
      control the RF output stage to output the electrosurgical waveform based on the impedance being lower than the impedance threshold and the change in impedance being lower than the upper change in impedance threshold.

2. The electrosurgical generator according to claim 1, wherein the controller is further configured to determine whether the change in impedance is less than a lower change in impedance threshold.

3. The electrosurgical generator according to claim 1, wherein the controller is further configured to:
   detect a phase shift of the electrosurgical waveform;
   determine whether the phase shift exceeds a phase shift threshold; and
   activate the alarm based on the phase shift determination.

4. The electrosurgical generator according to claim 2, wherein the controller is further configured to signal the RF output stage to output the electrosurgical waveform for a time period in response to the change in impedance being between the lower change in impedance threshold and the upper change in impedance threshold.

5. The electrosurgical generator according to claim 3, wherein the controller is further configured to:
   determine whether the phase shift exceeds the phase shift threshold; and
   activate the alarm in response to the phase shift exceeding the phase shift threshold.

6. A method of detecting whether jaws of an electrosurgical instrument are in a slow open condition, the method comprising:
   outputting through a radiofrequency (RF) output stage an electrosurgical waveform through the jaws of the electrosurgical instrument configured to grasp tissue;
   measuring an impedance of the tissue between the jaws;
   determining whether the impedance of the tissue disposed between the jaws exceeds an impedance threshold and whether a change in the impedance is greater than an upper change in impedance threshold;
   outputting an alarm indicative of the jaws being at least partially open based on the impedance exceeding the impedance threshold and on the change in impedance exceeding the upper change in impedance threshold; and
   controlling the RF output stage to output the electrosurgical waveform based on the impedance being lower than the impedance threshold and the change in impedance being lower than the upper change in impedance threshold.

7. The method according to claim 6, further comprising determining whether the change in impedance is less than a lower change in impedance threshold.

8. The method according to claim 6, further comprising:
   detecting a phase shift of the electrosurgical waveform;
   determining whether the phase shift exceeds a phase shift threshold; and
   activating the alarm based on the phase shift determination.

9. The method according to claim 7, further comprising outputting the electrosurgical waveform for a time period in response to the change in impedance being between the lower change in impedance threshold and the upper change in impedance threshold.

10. The method according to claim 8, further comprising:
    determining whether the phase shift exceeds the phase shift threshold; and
    activating the alarm in response to the phase shift exceeding the phase shift threshold.

11. A non-transitory computer-readable storage medium storing instructions which, when executed by a processor, cause an electrosurgical generator to:
    output through a radiofrequency (RF) stage an electrosurgical waveform through at least one pair of electrodes of an electrosurgical instrument;
    measure an impedance between the at least one pair of electrodes configured to grasp tissue;
    determine whether the impedance of the tissue disposed between the at least one pair of electrodes exceeds an impedance threshold and whether a change in the impedance is greater than an upper change in impedance threshold; and
    output an alarm indicative of the at least one pair of electrodes being at least partially open based on the impedance exceeding the impedance threshold and the change in impedance exceeding the upper change in impedance threshold; and control the RF output stage to output the electrosurgical waveform based on the impedance being lower than the impedance threshold and the change in impedance being lower than the upper change in impedance threshold.

12. The non-transitory computer-readable storage medium according to claim 11, wherein the instructions further cause the electrosurgical generator to determine whether the change in impedance is less than a lower change in impedance threshold.

13. The non-transitory computer-readable storage medium according to claim 11, wherein the instructions further cause the electrosurgical generator to:
  detect a phase shift of the electrosurgical waveform;
  determine whether the phase shift exceeds a phase shift threshold; and
  activate the alarm based on the phase shift determination.

14. The non-transitory computer-readable storage medium according to claim 12, wherein the instructions further cause the electrosurgical generator to output the electrosurgical waveform for a time period in response to the change in impedance being between the lower change in impedance threshold and the upper change in impedance threshold.

15. The non-transitory computer-readable storage medium according to claim 13, wherein the instructions further cause the electrosurgical generator to:
  determine whether the phase shift exceeds the phase shift threshold; and
  activate the alarm in response to the phase shift exceeding the phase shift threshold.

\* \* \* \* \*